(12) United States Patent
Wiedenbein

(10) Patent No.: US 11,771,438 B2
(45) Date of Patent: Oct. 3, 2023

(54) SURGICAL INSTRUMENT

(71) Applicant: Cardiomedical GMBH, Langenhagen (DE)

(72) Inventor: Wolfgang Wiedenbein, Langenhagen (DE)

(73) Assignee: Cardiomedical GMBH, Langenhagen (DE)

( * ) Notice: Subject to any disclaimer, the term of this patent is extended or adjusted under 35 U.S.C. 154(b) by 77 days.

(21) Appl. No.: 17/204,200

(22) Filed: Mar. 17, 2021

(65) Prior Publication Data

US 2022/0296245 A1 Sep. 22, 2022

(51) Int. Cl.
*A61B 17/122* (2006.01)
*A61B 17/28* (2006.01)
*A61B 17/00* (2006.01)

(52) U.S. Cl.
CPC ........ *A61B 17/122* (2013.01); *A61B 17/2804* (2013.01); *A61B 2017/0042* (2013.01); *A61B 2017/00407* (2013.01)

(58) Field of Classification Search
CPC .............. A61B 17/122; A61B 17/0482; A61B 17/2804; A61B 17/29; A61B 2017/0042; A61B 2017/00407; A61B 2017/00738; A61B 2017/2908; A61B 2017/291
See application file for complete search history.

(56) References Cited

U.S. PATENT DOCUMENTS 3,841,521 A * 10/1974 Jarvik .............. A61B 17/12013
                                                                                                      221/75
2015/0250484 A1* 9/2015 Salehi ................ A61B 17/1608
                                                                                                      606/83

FOREIGN PATENT DOCUMENTS

DE     202017004226 U1 * 11/2017 ........... A61B 17/122
EP        3441022 B1     8/2020

* cited by examiner

*Primary Examiner* — Shaun L David
*Assistant Examiner* — Rachael L Geiger
(74) *Attorney, Agent, or Firm* — Husch Blackwell LLP

(57) ABSTRACT

A surgical instrument is provided that may be used to occlude organic body parts during surgery. The surgical instrument is generally composed of an actuating device, a gripping device, and a joint system. The surgical instrument may be rotated about the joint system such that the actuating device can be pivoted out of the operating field during use. The actuating device can be used to transmit a pivoting movement and an actuating movement that operates the gripping device. The gripping device is constructed of gripping elements that can occlude organic body parts. The surgical instrument also includes a locking system that can prevent the rotation of the surgical instrument about the joint system. The locking system may also prevent the operation of the actuating device when the surgical instrument is pivoted about the joint system.

14 Claims, 4 Drawing Sheets

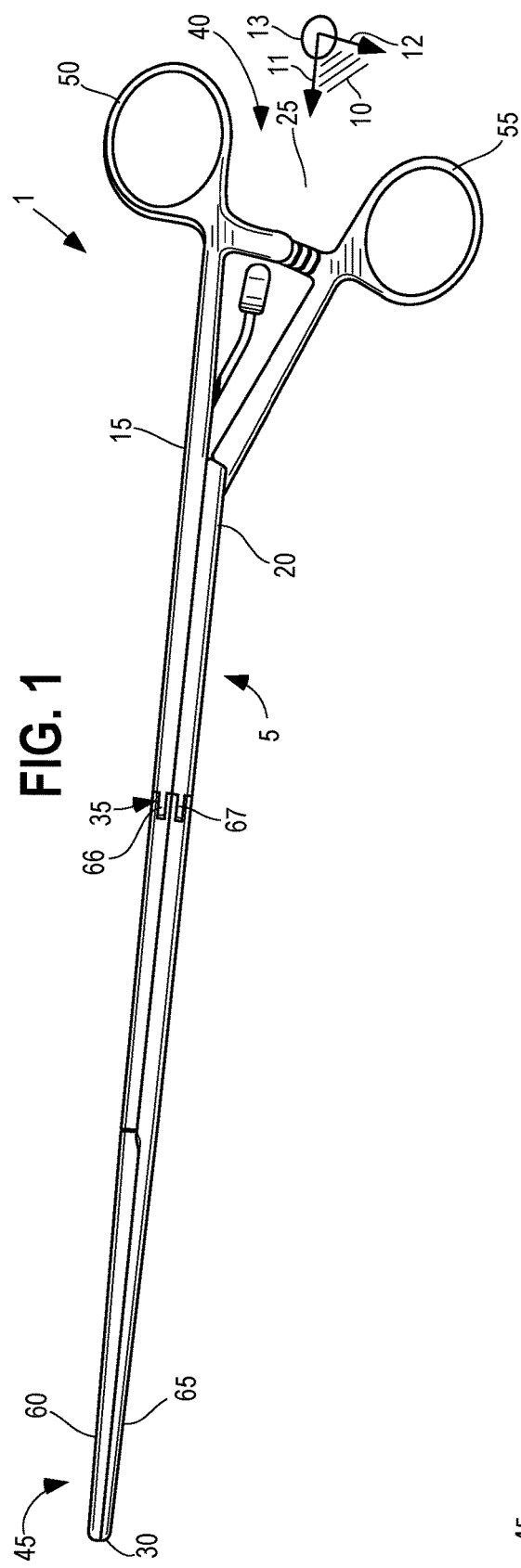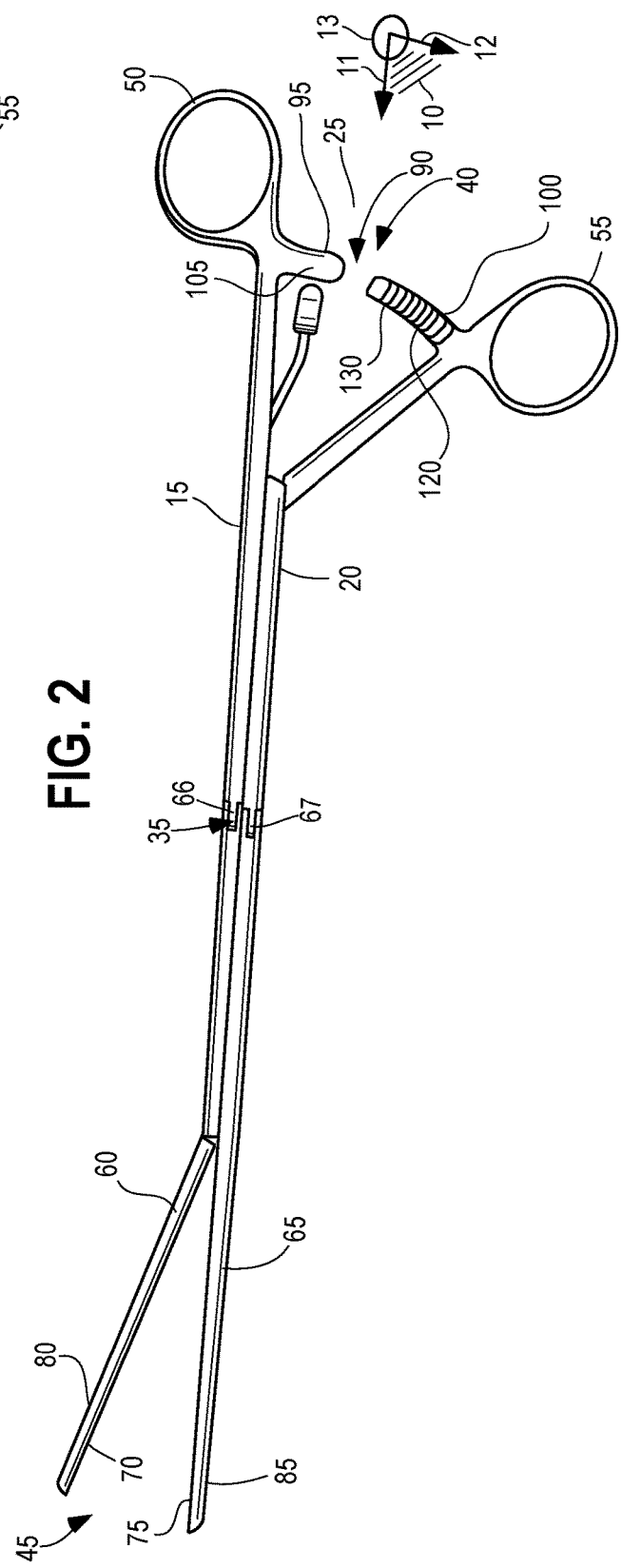

SURGICAL INSTRUMENT

FIELD OF THE INVENTION

The present invention relates generally to a medical instrument, and more particularly to a surgical clamp used by surgeons for occluding blood vessels and the like.

BACKGROUND OF THE INVENTION

In the surgical field, instruments, devices, or processes are used to examine the interior of living organisms and for surgical interventions. Surgical instruments include all medical instruments that are primarily used in surgery. A specific subcategory of surgical instruments, known as gripping or clamping instruments, are used for tying off or pressing together tubular- or hose-shaped body parts such as blood vessels. Gripping or clamping instruments commonly used in cardiac, thoracic, and vascular surgery are available in a wide variety of types and are well known in the art.

In an ordinary cardiac and thoracic surgery, an open operation is carried out in which access to the heart is created by opening the thorax. Typically, a surgeon may access the heart by means of a median sternotomy, which requires making a longitudinal incision approximately twenty-five (25) centimeters long through the sternum to open the chest. In a thoracotomy, a surgeon may further access the thorax through an intercostal incision, which is a small incision made in the space between the ribs. The opening created by the sternotomy or intercostal incision is kept open by means of a rib spreader, which expands the chest and keeps it open. Once the opening has been secured, the surgeon carries out interventions on organic body parts through the opening created in the chest with the help of a variety of different surgical instruments. For example, if the patient's heart is exposed, various catheters, cannulas, and clamps are placed directly on the heart and large blood vessels. Typically, the aorta is occluded around the ascending aorta with a hemostat to isolate the coronary arteries from the rest of the arterial system.

Instrument use during cardiothoracic surgery presents two problems. First, the surgical instruments occupy space within the surgical opening, effectively reducing the size of the opening. In turn, the reduced size of the surgical opening impedes the surgeon's field of vision within the operating field and hinders his or her work. Second, the size of the surgical opening and the associated tissue damage directly impacts how quickly a patient may recover from surgery. Thus, increasing the size of the surgical opening to accommodate traditional surgical instruments delays a patient's recovery from the surgery.

The latest developments in cardiac, thoracic, and vascular surgery relate to minimally invasive surgery techniques. Such techniques reduce the size of the surgical opening to reduce tissue damage and surgical trauma, facilitating faster patient recovery. Unfortunately for the surgeon, conventional surgical instruments placed in small access openings reduce the size of the surgeon's operating and visual field, making the operation more difficult, or sometimes impossible. Thus, minimally invasive surgery necessitates the use of surgical instruments that are adapted for use in smaller surgical openings.

As such, in minimally invasive surgeries, surgeons have turned to surgical clamps and gripping devices that occupy a smaller portion of the operating field. An example of such a device is illustrated in EP 3,441,022 B1. The instrument described in EP 3,441,022 B1 features an actuating device, a gripping device, and a joint arranged on an instrument shaft. The actuating device provides an interface through which the surgeon can operate the gripping device that is used to occlude blood vessels. The joint allows the surgeon to pivot the actuating end of the instrument out of his field of view. Since the surgeon has a better view of the operating field after pivoting the actuating end of the instrument, the surgeon can more easily carry out surgical interventions without increasing the size of the surgical opening. In addition, the device of EP 3,441,022 B1 features a locking system that prevents operation of the joint system. Only when the surgeon disengages the locking system may he or she pivot the actuating end of the instrument out of his field of view.

While the device described in EP 3,441,022 B1 is adapted for use in minimally invasive surgeries, its design presents issues that hinder its effectiveness. First, when the surgeon disengages the locking system, the gripping device is still capable of releasing its grip on the occluded body part. Thus, it is possible for a surgeon to accidently reopen the occluded body part when moving the actuating end of the device from his field of view. Accidently reopening an occluded body part could severely harm the patient. Second, the locking system in the prior art requires the surgeon use both of his hands to operate the instrument: one hand is needed to hold or maneuver the surgical instrument, and the surgeon's other hand is required to disengage the locking system.

Thus, the market calls for a surgical instrument in which the surgeon can, using only one hand, engage or disengage a locking system of the instrument while also ensuring that the surgeon does not reopen the occluded body part when the instrument is pivoted out of the surgical field.

SUMMARY OF THE INVENTION

The present invention is a surgical instrument capable of being operated with one hand by an operator such as a surgeon. The surgical instrument may occlude body parts and be maneuvered out of the surgeon's field of view during surgery. The surgical instrument may include an instrument shaft having an actuating device on a first end of the instrument shaft and a gripping device on the second end of the instrument shaft, opposite the first end. A joint system on the instrument shaft separates the two ends and provides a pivot point about which the surgical instrument may rotate. The gripping device may be composed of gripping elements that can occlude blood vessels, while the actuating device may feature handle elements that can be used by a surgeon to maneuver the instrument and operate the gripping elements of the gripping device.

Further, the surgical instrument is preferably equipped with a locking system. In one embodiment, the locking system may include a movable bolt. In at least one configuration, the movable bolt is positioned to prevent a pivoting movement about the joint system. In another configuration, the movable bolt is positioned to allow for operation of the joint system such that the surgeon may pivot the actuating device out of the surgical field. In some embodiments, when the moveable bolt is in a second position, it may also lock the handle elements of the actuating device in place, preventing the surgeon from disengaging the gripping elements and reopening an occluded body part.

To operate the surgical instrument, the surgeon may begin by placing the movable bolt in a first position to lock the joint system. Then, the surgeon may maneuver the surgical instrument inside the operating field. When the surgeon is ready to occlude a blood vessel, the surgeon may operate the actuating end of the instrument to open the gripping device. Next, the surgeon may maneuver the interior surfaces of the gripping elements around the blood vessel and close the gripping elements to occlude the vessel. Once the blood vessel is occluded, the surgeon may use a finger to displace the movable bolt from the first position to a second position. This action preferably locks the handle elements of the actuating device in place (preventing operation of the gripping device) and allows the surgeon to move the actuating end of the surgical instrument out of the field of view. Once the surgery is complete, the surgeon may remove the surgical instrument by reversing each of the steps previously described. Eventually, blood flow through the blood vessel may be restored.

BRIEF DESCRIPTION OF THE DRAWINGS

For a better understanding of the present invention, reference may be made to the following accompanying drawings.

FIG. 1 is a top plan view of a surgical instrument constructed according to the teachings of the present invention;

FIG. 2 is a top plan view of the surgical instrument of FIG. 1 when an actuating device and a gripping device of the surgical instrument are each in an open position;

DETAILED DESCRIPTION OF THE INVENTION

Figure 3:
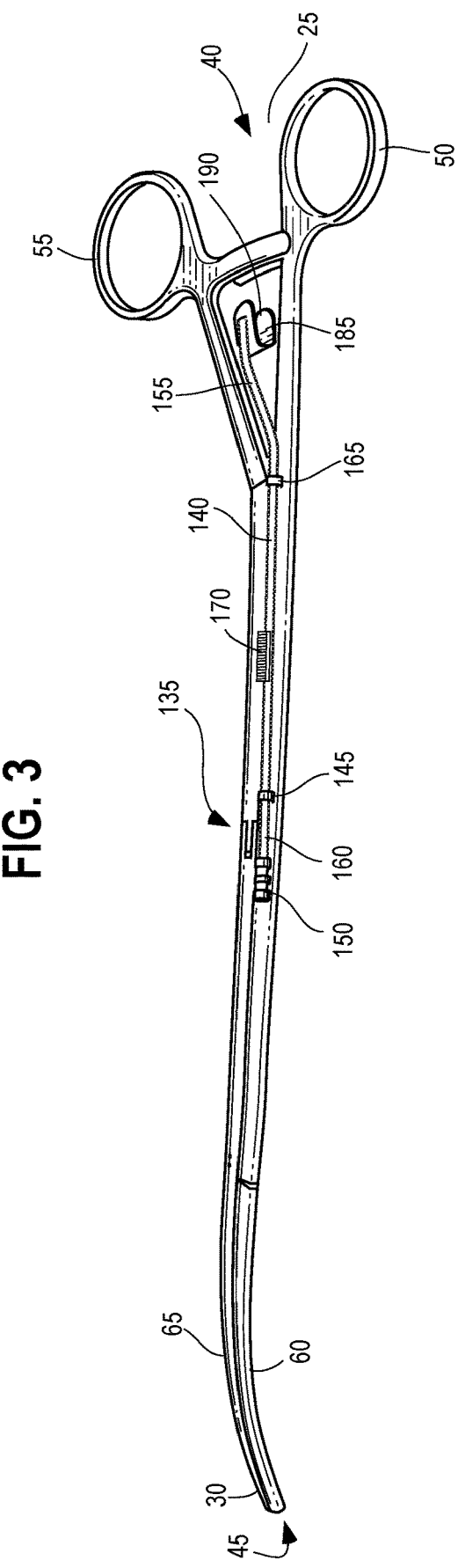
FIG. 3 is a bottom perspective view of the surgical instrument of FIG. 1.

The present invention will now be described with reference to the drawing figures, in which like reference numerals refer to like parts throughout. For purposes of clarity in illustrating the characteristics of the present invention, proportional relationships of the elements have not necessarily been maintained in the drawing figures.

FIG. 1 illustrates a surgical instrument 1 that may be used to occlude tubular- or hose-shaped body parts. As illustrated and described herein, the surgical instrument 1 is scaled for occluding blood vessels, specifically arteries, but in alternative embodiments it may be scaled for occluding other tube-shaped body parts, as would be appreciated by those skilled in the art.

As illustrated in FIG. 1, the surgical instrument 1 includes an instrument shaft 5 extending along a first axis 11.

The instrument shaft 5 is generally composed of a first branch 15, a second branch 20, a proximal end 25, and a distal end 30. The proximal end 25 and the distal end 30 of the surgical instrument 1 are separated by a joint system 35. In this embodiment, an actuating device 40 is located at the proximal end 25 and a gripping device 45 is located at the distal end 30 of the surgical instrument 1. The actuating device 40 is composed of handle elements 50 and 55 and the gripping device 45 is composed of gripping elements 60 and 65. The handle elements 50 and 55 of the actuating device extend along a plane 10 created by the first axis 11 and a second axis 12 that is perpendicular to the first axis 11.

The components of instrument shaft 5 allow an operator, such as a surgeon, to operate the actuating device 40 to transmit an actuating movement to operate the gripping device 45, both of which move along the plane 10, pivoting about a third axis 13 extending into and out of the page. Subsequently, an operator may remove the actuating device 40 from the operating field after the gripping device 45 occludes a blood vessel.

The gripping device in FIG. 1 is illustrated in a closed position. Operation of the actuating device 40 opens and closes the gripping device 45. More particularly, a surgeon may grasp the handle elements 50 and 55 to operate the actuating device 40. The handle element 50 may be integrally formed with the first branch 15. The handle element 55 may be movably connected to the first branch 15 via a fastener or connector and rotatably attached to the second branch 20 via a fastener or connecter, as would be appreciated by those skilled in the art. When operating the surgical instrument 1, the surgeon may apply a rotational force to the handle element 55 to operate the gripping device 45, both along the plane 10, about the third axis 13. The surgeon may instead apply a force perpendicular to the plane 10, causing a pivoting movement in a plane formed by the first axis 11 and the third axis 13, about the second axis 12 to pivot the actuating device 40 out of the operating field.

The pivoting motion about the second axis 12 of the actuating device 40 is facilitated by the joint system 35. The joint system 35 may be composed of a first joint 66 disposed on the first branch 15 and a second joint 67 disposed on the second branch 20. When the surgeon applies a rotational force about the second axis 12 to the actuating device 40, the actuating device 40 may rotate in the plane formed between the first axis 11 and the third axis 13. When rotation occurs about the joint system 35, the rotational force is applied to the joint system 35, such that the gripping device 45 does not shred or tear the occluded body part. Further, the joint system 35 is designed to be self-locking, so that the actuating device 40 can only be pivoted about the joint system 35 after the surgeon applies a force to the surgical instrument 1. Such joint systems that can effectuate the pivoting movement described here are well known in the art and the joint system illustrated herein is not limited to any particular embodiment.

Turning to FIG. 2, the gripping device 45 is illustrated in an open position. The gripping element 60 is movably arranged on the first branch 15 and rotatably connected to the second branch 20 via fasteners, such as bolts, screws, or pins, that are known by those skilled in the art. The gripping element 65 may be formed from one piece. When the surgeon applies a rotational force to the handle element 55 about the third axis 13, the handle element 55 rotates in a clockwise direction in the plane 10 away from the first axis 11. The applied rotational force is transmitted through the instrument shaft 5 to rotate the gripping element 60 in a clockwise direction in the plane 10 away from the first axis 11, thereby opening the gripping device 45.

As illustrated in FIG. 2, when the handle element 55 is at its greatest angle of rotation away from the first axis 11, the gripping element 60 is also at its maximum angle of rotation away from the first axis 11. As would be appreciated by those skilled in the art, the gripping device 45 may also be placed in a plurality of positions between its open and closed position by rotating the handle element 55 varying degrees of rotation away from the first axis 11.

When the handle element 55 rotates in a clockwise direction in the plane 10 away from the first axis 11, the first branch 15 and the first joint 66 may be displaced towards the proximal end 25. The second branch 20 and the second joint 67 may not be displaced as the handle element 55 rotates. As the first branch 15 is displaced towards the proximal end 25, the gripping element 60 may rotate in a clockwise direction in the plane 10 away from the first axis 11, opening the gripping device 45.

Each of the gripping elements 60 and 65 may have interior surfaces 70 and 75, and outer surfaces 80 and 85, respectively. When the gripping device 45 is in the open position, the surgeon may position a blood vessel between the interior surfaces 70 and 75 of gripping elements 60 and 65. After placing the blood vessel between the interior surfaces 70 and 75, the surgeon may use the actuating device 40 to place the gripping device 45 into the closed position, thus occluding the blood vessel. In some embodiments, the interior surfaces 70 and 75 may be coated with a non-abrasive material or equipped with a non-abrasive design to protect fragile blood vessels from tearing or other damage. To reopen the blood vessel, the surgeon may use the actuating device 40 to rotate the gripping element 60 in the clockwise direction in the plane 10 away from the first axis 11, returning the gripping device 45 to the open position.

In some embodiments, the actuating device may also be equipped with a ratchet system 90. The ratchet system 90 may include a first ratchet arm 95 and a second ratchet arm 100, which are preferably coupled to handle elements 50 and 55, respectively. The first ratchet arm 95 has an anterior surface 105 and a posterior surface 110 (illustrated in FIG. 5) and the second ratchet arm 100 has an anterior surface 115 (illustrated in FIG. 5) and a posterior surface 120. The posterior surface 105 of the first ratchet arm 95 may have a plurality of detent teeth 125 facing a first direction, and the posterior surface 120 of the second ratchet arm 100 may have a plurality of detent teeth 130 facing a second direction. When the actuating device 40 is in the closed position, the detent teeth 125 of the first ratchet arm 95 and the detent teeth 130 of the second ratchet arm 100 preferably engage with one another. The engagement of the detent teeth 125 and 130 prevents the handle element 55 from rotating in the clockwise direction in the plane 10 away from the first axis 11, thus temporarily locking the actuating device 40 in place. This in turn prevents the operation of the gripping device 45. To disengage the detent teeth 125 and 130, and thereby disengage the ratchet system 90, the surgeon may use his palm to apply a force in the direction of the third axis 13, lifting the detent teeth 125 and 130 out of alignment. Further, the surgeon may selectively engage each individual tooth of the detent teeth 125 and 130 to incrementally adjust the position of the handle element 55, which in turn incrementally adjusts the gripping device 45 within the open and closed positions.

FIG. 3 illustrates an embodiment of a locking system 135 of the surgical instrument 1. The locking system 135, when in a first position (as illustrated in FIG. 3) prevents the rotation of the surgical instrument 1 about the joint system 35. In the first position, the locking system 135 may keep the actuating device 40 and gripping device 45 of the surgical instrument 1 aligned with the first axis 11.

In the embodiment illustrated in FIG. 3, the locking system 135 is generally composed of a movable bolt 140 and raised ring structures 145 and 150. Generally, the movable bolt has a proximal end 155 and a distal end 160. When the movable bolt 140 is in the first position, a portion of the distal end 160 extends into the raised ring structures 145 and 150 and over the joint system 35. The remaining portion of the movable bolt 140 lies over the proximal end 25 of the instrument shaft 5. When a force is applied to the movable bolt 140 toward the proximal end 155, the moveable bolt 140 can slide towards the actuating device 40 and into a second position. When in the second position, the distal end of the movable bolt 140 is no longer within the raised ring structure 145 nor over the joint system 35. The movable bolt 140 may be returned to the first position by sliding it towards the distal end 30 of the instrument shaft 5. To further secure the movable bolt 140 such that it is aligned with the first branch 15, a third raised ring structure 165 may be positioned near the actuating device 40. Other constructions of locking systems equivalent to the one described here would be appreciated by those skilled in the art. As also illustrated in FIG. 3, the movable bolt 140 may include raised grooves 170.

Preferably, the raised grooves 170 are located near the midpoint of the movable bolt 140 or on the proximal end 155. The raised grooves 170 facilitate one-handed operation of the surgical instrument 1 by providing a surface that facilitates the generation of a static frictional force between the movable bolt 140 and the surgeon's finger. The static frictional force helps ensure that the surgeon's finger does not slip from the movable bolt 140 as the surgeon slides the movable bolt 140. Further, the raised grooves 170 may be positioned to facilitate one-handed operation of the surgical instrument 1 by ensuring that the raised grooves 170 are within reach of a finger of the hand the surgeon uses to grip the actuating device 40.

Figure 4:
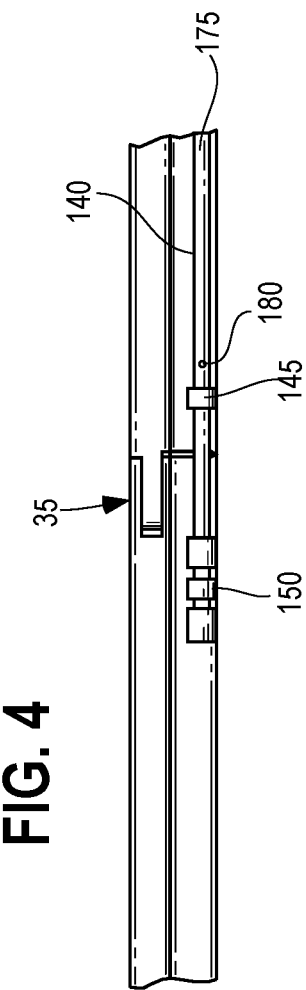
FIG. 4 is an enlarged view of a portion of a locking system of the surgical instrument of FIG. 1 when the locking system is in a first position.

As illustrated in FIG. 4, the raised ring structures 145 and 150 may be placed near the joint system 35. Preferably, if a plurality of rings is used for the raised ring structures 145 and 150, only a small amount of space is placed between each individual ring. The embodiment illustrated in FIG. 4 includes one raised ring within the raised ring structure 145 and three raised rings within the raised ring structure 150. However, in alternative embodiments more or fewer raised rings may be provided to guide the movable bolt 140 and keep the movable bolt 140 aligned with the instrument shaft 5, as would be appreciated by those skilled in the art.

In a preferred embodiment, the motion of the movable bolt 140 along the first axis 11 is restricted. By restricting the motion of the movable bolt 140 along the first axis 11, a surgeon may be prevented from disconnecting the movable bolt 140 from the surgical instrument 1. As illustrated in FIG. 4, the movable bolt 140 has a posterior surface 175. The posterior surface 175 of the movable bolt 140 may include a raised protrusion 180. When the movable bolt 140 is in the first position, the raised protrusion 180 engages with the raised ring structure 145 to prevent the movable bolt 140 from sliding any farther towards the distal end 30 of the instrument shaft 5. Advantageously, restricting the sliding motion of the movable bolt 140 towards the distal end 30 also prevents the raised grooves 170 from moving beyond the reach of the surgeon's fingers, which could impede one-handed operation of the surgical instrument 1.

Figure 5:
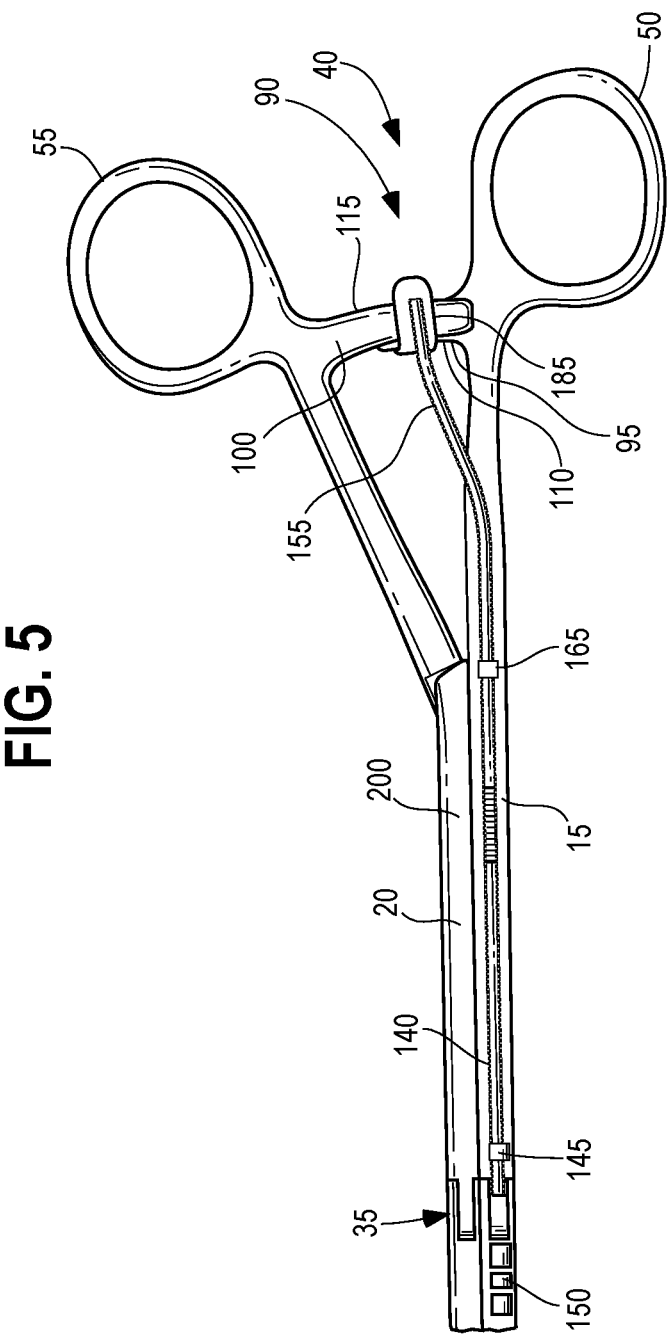
FIG. 5 is a partial bottom plan view of the surgical instrument of FIG. 1 when the locking system is in a second position.

The ability of the movable bolt 140 to slide towards the proximal end 25 of the instrument shaft 5 may also be restricted. As illustrated in FIG. 5, the proximal end 155 of the movable bolt 140 may feature a lip element 185 having an interior surface 190 (illustrated in FIG. 3). When the actuating device 40 is closed and the movable bolt 140 is in the second position, the interior surface 190 of the lip element 185 may engage with the ratchet system 90. Specifically, the interior surface 190 may engage with the anterior surface 105 of the first ratchet arm 95 and the anterior surface 115 of the second ratchet arm 100. Once the lip element 185 is engaged with the ratchet system 90, the movable bolt 140 may not slide any farther towards the proximal end 25 of the instrument shaft 5.

Advantageously, the engagement of the lip element 185 with the ratchet system 90 helps to prevent the surgeon from inadvertently disengaging the ratchet system 90, which in turn prevents rotation of the handle element 55 in the clockwise direction in the plane 10 away from the first axis 11. Thus, when the lip element 185 is engaged with the ratchet system 90, the surgeon need not worry about accidently freeing the occluded blood vessel from the gripping device 45.

Other constructions of the proximal end 155 of the movable bolt 140 that function in the same manner as the lip element 185 described above would be appreciated by those skilled in the art. In addition, there are alternative embodiments of the invention with regards to the position of the locking system 135 on the surgical instrument 1. In the embodiment captured in FIG. 5, the instrument shaft 5 of the surgical instrument 1 has an anterior surface 195 (not shown) and a posterior surface 200. In FIG. 5, the movable bolt 140 and raised ring structures 145, 150, and 165 are affixed to the posterior surface 200 of the instrument shaft 5 and to the first branch 15. However, the locking system 135 may be located on the second branch 20, or the anterior or posterior surface of the instrument shaft 5, as would be appreciated by those skilled in the art.

Figure 6:
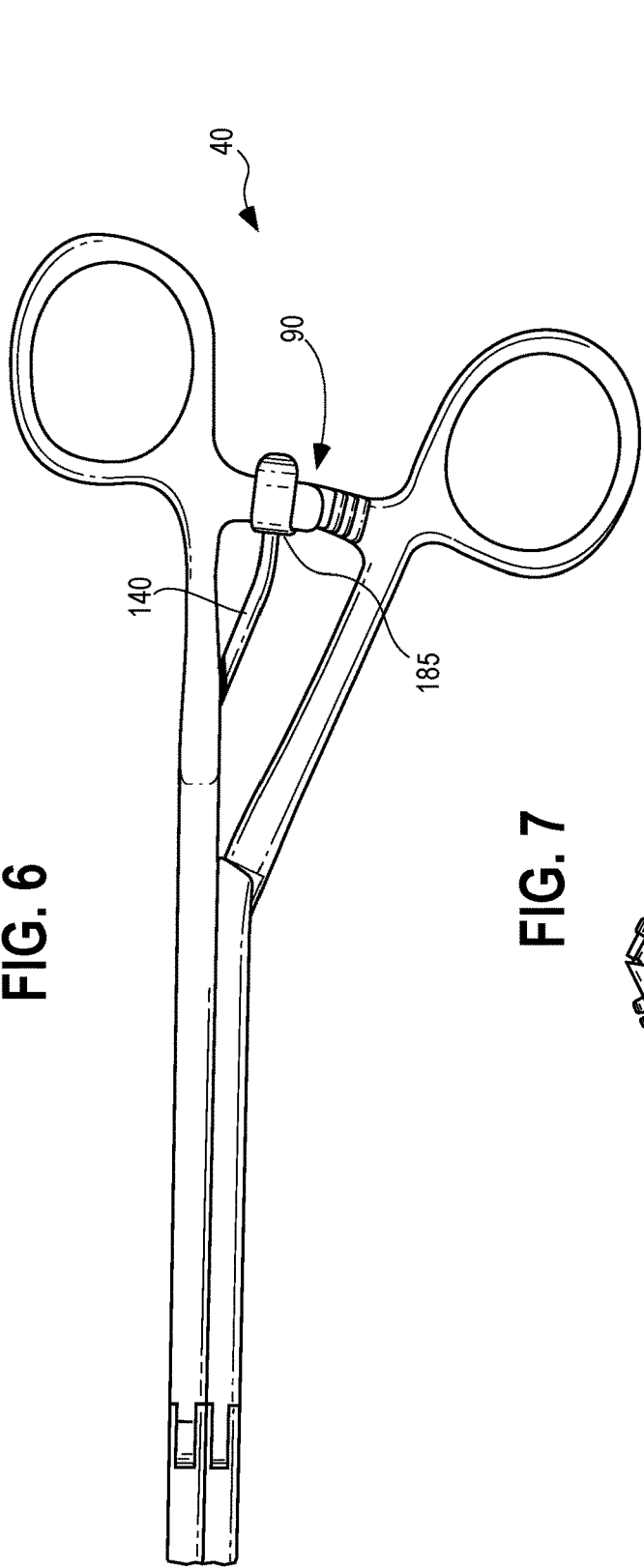
FIG. 6 is a partial top plan view of the surgical instrument of FIG. 1 when the locking system is in the second position.

FIG. 6 illustrates the engagement of the lip element 185 and the ratchet system 90 from a top view of the surgical instrument 1. In this figure, like in FIG. 5, the actuating device 40 is closed and the movable bolt 140 is in the second position.

Figure 7:
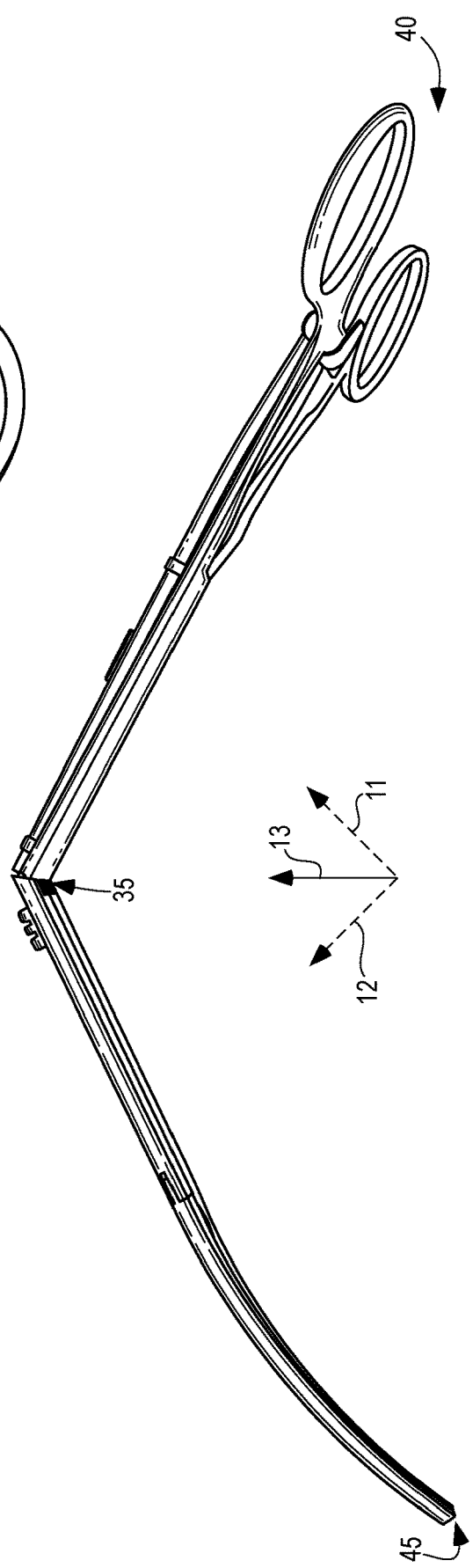
FIG. 7 is a side-perspective view of the surgical instrument of FIG. 1 where the actuating device of the instrument is pivoted about a joint system of the surgical instrument.

Once the surgeon has occluded a blood vessel, he may desire to pivot the actuating device 40 out of his field of view. The pivoting ability of the joint system 35, illustrated in FIG. 7, is especially important in minimally invasive surgeries since the surgeon's field of view is very restricted as compared to traditional surgery. In FIG. 7, the actuating device 40 is not in the plane 10 (not illustrated) between the first and second axes 11 and 12, and the position of the actuating device 40 on the third axis 13 has changed relative to its position before its rotation about the joint system 35. Thus, in the configuration illustrated in FIG. 7, the actuating device may no longer be in the surgeon's field of view.

At the end of the surgery, the surgical instrument 1 is typically removed from the surgical opening. To do so, the surgeon may first maneuver the actuating device 40 so that it is in alignment with the first axis 11. Then, the surgeon may return the movable bolt 140 to the first position to prevent rotation about the joint system 35. Once the movable bolt 140 is returned to the first position, the surgeon may use the actuating device 40 to open the gripping device 45, freeing the occluded blood vessel. The surgeon may then remove the surgical instrument 1 from the operating field.

From the foregoing, it will be seen that the various embodiments of the present invention are well adapted to attain all the objectives and advantages hereinabove set forth together with still other advantages which are obvious and which are inherent to the present structures. It will be understood that certain features and sub-combinations of the present embodiments are of utility and may be employed without reference to other features and sub-combinations. Since many possible embodiments of the present invention may be made without departing from the spirit and scope of the present invention, it is also to be understood that all disclosures herein set forth or illustrated in the accompanying drawings are to be interpreted as illustrative only and not limiting. The various constructions described above and illustrated in the drawings are presented by way of example only and are not intended to limit the concepts, principles, and scope of the present invention.

Many changes, modifications, variations, and other uses and applications of the present invention will, however, become apparent to those skilled in the art after considering the specification and the accompanying drawings. All such changes, modifications, variations, and other uses and applications which do not depart from the spirit and scope of the invention are deemed to be covered by the invention, which is limited only by the claims which follow.

What is claimed is:

1. A surgical instrument for occluding tubular organic body parts, the surgical instrument comprising:
    an instrument shaft including:
        a first branch;
        a second branch; and
        a joint system between a proximal end and a distal end of the surgical instrument, wherein the instrument shaft is pivotable about the joint system;
    a gripping device located at the distal end of the surgical instrument for selectively occluding tubular organic body parts, the gripping device comprising:
        a first gripping element arranged on the first branch; and
        a second gripping element arranged on the second branch;
    an actuating device located at the proximal end of the surgical instrument, the actuating device in mechanical connection with the gripping device via at least the instrument shaft, the actuating device configured to open and close the gripping device;
    a locking system extending along at least a portion of the instrument shaft;
    wherein when the locking system is in a first position, the locking system prevents the surgical instrument from being pivotable around the joint system; and
    wherein when the locking system is in a second position, the surgical instrument is pivotable around the joint system, and the actuating device is unable to open or close the gripping device;
    wherein the actuating device further includes:
    a first handle element being formed in one piece with the first branch of the instrument shaft;
    a second handle element being movably arranged on the second branch of the instrument shaft; and
    a ratchet system composed of a first arm and a second arm, wherein:
        the first arm is attached to the first handle element;
        the second arm is attached to the second handle element; and
        the first arm and the second arm include detent teeth that selectively engage with each other to lock the first handle element and the second handle element in predetermined positions;
    wherein the locking system further includes a movable bolt with a proximal end and a distal end;
    wherein the locking system further includes one or more raised ring structures on the proximal end of the instrument shaft near the joint system; and the movable bolt is inserted through at least one raised ring structure of the one or more raised ring structures on the proximal end of the instrument shaft near the joint system; and wherein the movable bolt further includes a raised protrusion capable of engaging a raised ring structure to prevent the sliding of the movable bolt in the distal direction beyond a predetermined point.

2. The surgical instrument of claim 1, wherein the proximal end of the movable bolt further includes a lip element which may engage with the ratchet system of the actuating device to prevent operation of the actuating device when the movable bolt is in the second position.

3. The surgical instrument of claim 1, wherein:

the locking system further includes one or more raised ring structures on the distal end of the instrument shaft near the joint system; and the movable bolt is inserted through at least one raised ring structure of the one or more raised ring structures on the distal end of the instrument shaft near the joint system.

4. The surgical instrument of claim 1, wherein the movable bolt further includes a raised groove portion.

5. The surgical instrument of claim 1, wherein:

the locking system further includes one or more raised ring structures on the proximal end of the instrument shaft near the actuating device such that when the movable bolt is inserted through at least one raised ring structure of the one or more raised ring structures on the proximal end of the instrument shaft near the actuating device, at least one raised ring structure of the one or more raised ring structures on the proximal end of the instrument shaft near the actuating device prevents the movable bolt from sliding out of alignment with the instrument shaft.

6. The surgical instrument of claim 1, wherein the gripping elements further include a non-abrasive surface.

7. A surgical instrument for occluding tubular organic body parts, the surgical instrument comprising:

an instrument shaft including:
 a proximal end;
 a distal end;
 a joint system between the proximal end and the distal end of the surgical instrument;
 a first surface between the proximal end and the joint system; and
 a second surface between the distal end and the joint system;

an actuating device at the proximal end of the surgical instrument;

a gripping device at the distal end of the surgical instrument, the gripping device in mechanical connection with the actuating device;

a locking system including a movable bolt composed of an elongated body affixed to the instrument shaft;

wherein the elongated body of the movable bolt has a proximal end and a distal end;

wherein when the locking system is in a first position, the distal end of the elongated body of the movable bolt extends towards the distal end of the surgical instrument past the joint system;

wherein when the locking system is in a second position, the distal end of the elongated body of the movable bolt abuts the first surface of the instrument shaft;

wherein the actuating device further includes a first handle element integrally formed with the instrument shaft and a second handle element movably arranged on the instrument shaft; and wherein the proximal end of the movable bolt further includes a lip element capable of locking the first handle element and the second handle element in a predetermined position to prevent operation of the actuating device.

8. The surgical instrument of claim 7, wherein:

the actuating device further includes a ratchet system, the ratchet system comprising:
 a first arm attached to the first handle element, the first arm including a surface having detent teeth; and
 a second arm attached to the second handle element, the second arm including a surface having detent teeth; and wherein the detent teeth of the first arm and the detent teeth of the second arm are selectively engageable to lock the first handle element and the second handle element in predetermined positions.

9. The surgical instrument of claim 8, wherein:

the first arm of the ratchet system further includes an anterior and a posterior surface and the second arm of the ratchet system further includes an anterior and a posterior surface;

the proximal end of the moveable bolt further includes a lip element with an interior surface; and the interior surface of the lip element of the movable bolt abuts both the posterior surface of the first arm of the ratchet system and the posterior surface of the second arm of the ratchet system to lock the first handle element and the second handle element of the actuating device in a predetermined position when the movable bolt is placed in a predetermined position.

10. The surgical instrument of claim 9, wherein the interior surface of the lip element of the movable bolt abuts the posterior surface the first arm of the ratchet system and the posterior surface of the second arm of the ratchet system only when the locking system is in the second position.

11. The surgical instrument of claim 9, wherein the locking system further includes one or more raised ring structures.

12. The surgical instrument of claim 11, wherein the movable bolt is inserted through at least one raised ring structure of the one or more raised ring structures.

13. The surgical instrument of claim 7, wherein the gripping device further includes one or more gripping elements.

14. The surgical instrument of claim 7, wherein the gripping device further includes a non-abrasive surface.

* * * * *